US012646307B2

(12) United States Patent
Zhang

(10) Patent No.:  US 12,646,307 B2
(45) Date of Patent:       Jun. 2, 2026

(54) METHOD FOR ACQUIRING TARGET MODEL, METHOD FOR DETERMINING PROGNOSIS EVALUATION VALUE, APPARATUSES, DEVICE, AND MEDIUM

(71) Applicant: BOE Technology Group Co., Ltd., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 261 days.

(21) Appl. No.:    18/702,096

(22) PCT Filed:    Jul. 31, 2023

(86) PCT No.:    PCT/CN2023/110353
§ 371 (c)(1),
(2) Date:    Apr. 17, 2024

(87) PCT Pub. No.: WO2024/066722
PCT Pub. Date: Apr. 4, 2024

(65) Prior Publication Data
US 2024/0412496 A1      Dec. 12, 2024

(30) Foreign Application Priority Data

Sep. 27, 2022    (CN) .......................... 202211186768.3

(51) Int. Cl.
*G06V 10/00*          (2022.01)
*A61B 5/00*          (2006.01)
(Continued)

(52) U.S. Cl.
CPC ............ *G06V 10/806* (2022.01); *A61B 5/055* (2013.01); *A61B 5/7275* (2013.01);
(Continued)

(58) Field of Classification Search
CPC ............ G06V 10/806; G06V 10/7715; G06V 10/774; G06V 2201/031; G06V 10/77;
(Continued)

(56) References Cited

U.S. PATENT DOCUMENTS

2009/0181384 A1*   7/2009  Nekarda .............. C12Q 1/6886
                                                435/6.14
2014/0011861 A1*   1/2014  McClelland ......... C12Q 1/6886
                                                435/6.14
(Continued)

FOREIGN PATENT DOCUMENTS

CN          110491479 A    11/2019
CN          113870259 A    12/2021
(Continued)

*Primary Examiner* — Van D Huynh
(74) *Attorney, Agent, or Firm* — WHDA, LLP

(57)                ABSTRACT

Provided is a method for acquiring a target model, including: acquiring sample groups corresponding to sample users, the sample group including sample information of multiple modalities; performing iterative trainings on a preset model based on the sample groups to obtain the target model, the target model being configured to predict a prognosis evaluation value of a target object, in each iterative training, feature extraction is performed on the sample information of the multiple modalities in a current sample group using the preset model, a predicted prognosis evaluation value and a consistency expression value are determined based on extracted sample features, the consistency expression value is used for characterizing a consistency degree of the sample features corresponding to a same target disease; and parameters of the preset model are updated based on the predicted prognosis evaluation value, a prognosis evaluation label corresponding to the current sample group, the consistency expression value.

19 Claims, 4 Drawing Sheets

(51) Int. Cl.

| | |
|---|---|
| *A61B 5/055* | (2006.01) |
| *G06T 7/00* | (2017.01) |
| *G06V 10/77* | (2022.01) |
| *G06V 10/774* | (2022.01) |
| *G06V 10/80* | (2022.01) |
| *G16B 20/00* | (2019.01) |
| *G16H 50/20* | (2018.01) |

(52) U.S. Cl.
CPC ........ *G06T 7/0012* (2013.01); *G06V 10/7715* (2022.01); *G06V 10/774* (2022.01); *G16B 20/00* (2019.02); *G16H 50/20* (2018.01); *G06T 2207/10088* (2013.01); *G06T 2207/20081* (2013.01); *G06T 2207/30016* (2013.01); *G06T 2207/30096* (2013.01); *G06V 2201/031* (2022.01)

(58) Field of Classification Search
CPC ...... G06V 10/80; A61B 5/055; A61B 5/7275; G06T 7/0012; G06T 2207/10088; G06T 2207/20081; G06T 2207/30016; G06T 2207/30096; G06T 7/00; G16B 20/00; G16H 50/20; G16H 30/40; G16H 50/70; G16H 50/50; G06F 17/16
See application file for complete search history.

(56) References Cited

U.S. PATENT DOCUMENTS

| | | | |
|---|---|---|---|
| 2020/0211209 A1* | 7/2020 | Liao | G06T 7/55 |
| 2021/0174958 A1* | 6/2021 | Drake | G06N 20/10 |
| 2022/0044762 A1* | 2/2022 | Van Der Baan | G16H 50/20 |
| 2022/0383626 A1* | 12/2022 | Wang | G06V 10/803 |
| 2023/0360758 A1* | 11/2023 | Casale | G06T 7/0012 |
| 2024/0221359 A1* | 7/2024 | Jin | G06V 10/44 |
| 2024/0233334 A1* | 7/2024 | Xia | G06T 5/60 |

FOREIGN PATENT DOCUMENTS

| | | |
|---|---|---|
| CN | 114121291 A | 3/2022 |
| CN | 114708465 A | 7/2022 |
| CN | 115762796 A | 3/2023 |
| EP | 4432219 A1 | 9/2024 |

* cited by examiner

METHOD FOR ACQUIRING TARGET MODEL, METHOD FOR DETERMINING PROGNOSIS EVALUATION VALUE, APPARATUSES, DEVICE, AND MEDIUM

CROSS-REFERENCE TO RELATED APPLICATION

This application claims priority to Chinese Patent Application No. 202211186768.3, entitled "METHOD FOR ACQUIRING TARGET MODEL, METHOD FOR DETERMINING PROGNOSIS EVALUATION VALUE, APPARATUSES, DEVICE, AND MEDIUM", filed to China National Intellectual Property Administration on Sep. 27, 2022, the entire contents of which are incorporated herein by reference.

TECHNICAL FIELD

The present disclosure relates to the technical field of information processing, and particularly to a method for acquiring a target model, a method for determining a prognosis evaluation value, an apparatus, a device, and a medium.

BACKGROUND

Brain gliomas originate from neuroglial cells and are the most common tumors of the central nervous system, accounting for approximately 50%~60% of intracranial tumors. The incidence shows an increasing trend annually. Patients with brain gliomas typically require prognosis evaluation after the surgery.

In the prognosis evaluation, the traditional prognosis is based on predictive factors such as the size and range of the lesion site, which has certain limitations.

SUMMARY

The present disclosure provides a method for acquiring a target model, including:

acquiring a plurality of sample groups, wherein each of the sample groups corresponds to a sample user, and includes sample information of multiple modalities, and the sample information of the multiple modalities includes at least two of a magnetic resonance (MR) sample image, clinical sample information, and gene sample information; and obtaining a target model by performing iterative trainings on a preset model based on the plurality of sample groups, the target model is used for predicting a prognosis evaluation value of a target object, each of the iterative trainings includes:

performing, by using the preset model, feature extraction on the sample information of the multiple modalities in a current sample group respectively, and determining a predicted prognosis evaluation value and a consistency expression value based on extracted sample features, wherein the consistency expression value is used for characterizing a consistency degree of the sample features corresponding to a same target disease; and updating parameters of the preset model based on the predicted prognosis evaluation value, a prognosis evaluation label corresponding to the current sample group, and the consistency expression value.

In an alternative embodiment, the updating parameters of the preset model based on the predicted prognosis evaluation value, a prognosis evaluation label corresponding to the current sample group, and the consistency expression value includes:

acquiring a difference between the predicted prognosis evaluation value and the prognosis evaluation label; and updating the parameters of the preset model with a target of minimizing the difference and maximizing the consistency expression value.

In an alternative embodiment, the updating the parameters of the preset model with a target of minimizing the difference and maximizing the consistency expression value includes:

constructing a loss function based on the difference and the consistency expression value as follows:

$$\text{loss} = \sum_i (y_i' - y_i)^2 - \text{consistency};$$

updating, based on a loss value of the loss function, the parameters of the preset model with the target of minimizing the difference and maximizing the consistency expression value, the 'loss' represents the loss value, $y'_i$ represents the predicted prognosis evaluation value, $y_i$ represents the prognosis evaluation label, and 'consistency' represents the consistency expression value.

In an alternative embodiment, the determining the consistency expression value based on extracted sample features includes:

transposing each of the sample features, and obtaining transposed features corresponding to various sample features;

for two different sample features, fusing one of the two sample features with the transposed feature corresponding to the other sample feature, and obtaining a corresponding fused feature value; and determining the consistency expression value based on each fused feature value.

In an alternative embodiment, the sample information of each modality includes a plurality of sub-sample information, and the performing, by using the preset model, feature extraction on the sample information of the multiple modalities in a current sample group includes:

for the sample information of each modality, performing feature extraction on the plurality of sub-sample information in the sample information of the modality, and obtaining a plurality of sub-feature vectors corresponding to the plurality of sub-sample information; and obtaining a sample feature corresponding to the sample information of the modality by performing feature fusion on the plurality of sub-feature vectors corresponding to the sample information of each modality.

In an alternative embodiment, the obtaining a sample feature corresponding to the sample information of the modality by performing feature fusion on the plurality of sub-feature vectors corresponding to the sample information of each modality includes:

determining an attention value between every two sub-feature vectors, the attention value is used for characterizing a degree of closeness between the two sub-feature vectors; and obtaining the sample feature corresponding to the sample information of the modality by fusing the plurality of sub-feature vectors based on the attention value.

In an alternative embodiment, the obtaining the sample feature corresponding to the sample information of the modality by fusing the plurality of sub-feature vectors based on the attention value includes:

for each sub-feature vector, fusing all the other sub-feature vectors into the sub-feature vector based on attention values between the sub-feature vector and all the other sub-feature vectors, and obtaining a fused sub-vector for the sub-feature vector; and obtaining the sample feature corresponding to the sample information of the modality by performing re-fusion on a plurality of fused sub-vectors.

In an alternative embodiment, the parameters of the preset model include a first parameter matrix, the MR sample image includes a plurality of slice sample images, and the determining an attention value between every two sub-feature vectors includes: for each slice sample image included in the MR sample image, determining an attention value between sub-feature vectors corresponding to every two slice sample images based on a current value of the first parameter matrix.

In an alternative embodiment, the parameters of the preset model includes a second parameter matrix and a third parameter matrix, and the obtaining a sample feature corresponding to the sample information of the modality by performing feature fusion on the plurality of sub-feature vectors corresponding to the sample information of each modality includes:

for each piece of clinical sub-sample information in the clinical sample information, performing feature fusion on sub-feature vectors corresponding to the clinical sub-sample information based on a current value of the second parameter matrix, and obtaining a sample feature corresponding to the clinical sample information; and for each piece of gene sub-sample information in the gene sample information, performing feature fusion on sub-feature vectors corresponding to the gene sub-sample information based on a current value of the third parameter matrix, and obtaining a sample feature corresponding to the gene sample information.

In an alternative embodiment, the parameters of the preset model include a parameter set corresponding to the clinical sample information, the clinical sample information includes numerical sub-sample information and non-numerical sub-sample information, and the performing, by using the preset model, feature extraction on the sample information of the multiple modalities in a current sample group includes:

for the clinical sample information in the current sample group, converting the non-numerical sub-sample information into a first sub-feature vector;

obtaining a corresponding second sub-feature vector by mapping, based on a current value of each parameter in the parameter set, the numerical sub-sample information to a target space, the parameters in the parameter set are used for determining a dimension of the target space and a value at each spatial point; and obtaining a sample feature corresponding to the clinical sample information by fusing the first sub-feature vector and the second sub-vector.

In an alternative embodiment, the parameter set includes a first parameter vector, a second parameter vector, and a fourth parameter matrix, and the obtaining a corresponding second sub-feature vector by mapping, based on a current value of each parameter in the parameter set, the numerical sub-sample information to a target space includes:

mapping the numerical sub-sample information to a first dimension in the target space based on a current value of the first parameter vector to obtain a mapping value of the first dimension, the first parameter vector is used for determining a value of a spatial point of the target space in the first dimension; and determining the second sub-feature vector based on the mapping value of the first dimension, a current value of the second parameter vector, and a current value of the fourth parameter matrix, wherein the second parameter vector is used for determining a value of a spatial point of the target space in a second dimension, and the fourth parameter matrix is used for assigning a parameter to each spatial position in the first dimension and the second dimension.

In an alternative embodiment, the parameter set further includes a plurality of third parameter vectors, and after determining the second sub-feature vector based on the mapping value of the first dimension, the current value of the second parameter vector, and the current value of the fourth parameter matrix, the method further includes:

correcting, based on the second sub-feature vector and the plurality of third parameter vectors, the second sub-feature vector according to a formula as follows:

$$va = \frac{e^{(sa^T \cdot a_1)}}{\sum_{i=1}^{3} e^{(sa^T \cdot a_i)}} \times a_1 + \frac{e^{(sa^T \cdot a_2)}}{\sum_{i=1}^{3} e^{(sa^T \cdot a_i)}} \times a_2 + \frac{e^{(sa^T \cdot a_3)}}{\sum_{i=1}^{3} e^{(sa^T \cdot a_i)}} \times a_3,$$

va is a corrected second sub-feature vector, sa is the second sub-feature vector, and a1, a2, and a3 are the third parameter vectors; and the obtaining a sample feature corresponding to the clinical sample information by fusing the first sub-feature vector and the second sub-vector includes:

obtaining the sample feature corresponding to the clinical sample information by fusing the first sub-feature vector and the corrected second sub-vector.

In an alternative embodiment, the parameters of the preset model include a dimension parameter matrix corresponding to sample information of each modality, and the determining a predicted prognosis evaluation value and a consistency expression value based on extracted sample features includes:

obtaining a converted sample feature by performing, based on the sample feature and the dimension parameter matrix corresponding to the sample information of each modality, dimension transformation on the sample feature corresponding to the sample information of the modality; and determining the predicted prognosis evaluation value and the consistency expression value based on converted sample features corresponding to each piece of the sample information of the multiple modalities.

In an alternative embodiment, the preset model includes a fusion module, a prediction branch, a consistency expression branch, and data processing modules corresponding to sample information of the modalities, and the performing, by using the preset model, feature extraction on the sample information of the multiple modalities in a current sample group, and determining a predicted prognosis evaluation value and a consistency expression value based on extracted sample features includes:

for the sample information of each modality in the current sample group, performing feature extraction on corresponding sample information using a data processing module corresponding to the sample information of the modality;

fusing sample features output by the data processing modules using the fusion module;

determining, using the prediction branch, the predicted prognosis evaluation value corresponding to a feature output by the fusion module; and determining, using the consistency expression branch, the consistency expression value corresponding to the sample features output by the data processing modules.

An embodiment of the present disclosure provides a method for determining a prognosis evaluation value, including:

acquiring information of multiple modalities of an object to be measured, the information of the multiple modalities includes a magnetic resonance (MR) image, clinical information, and gene information; and obtaining a prognosis evaluation value of the object to be measured by inputting the information of the multiple modalities into a target model, the target model is obtained according to the method for acquiring a target model.

The above description is merely a summary of the technical solution of the present disclosure, which may be implemented in accordance with the contents of the specification in order to make the technical means of the present disclosure more clearly understood, and in order to make the above and other objects, features, and advantages of the present disclosure more apparent, specific implementations of the present disclosure are set forth below.

BRIEF DESCRIPTION OF THE DRAWINGS

In order to describe technical solutions of the embodiments of the present disclosure or the related art more clearly, the accompanying drawings used in the illustration of the embodiments or the related art will be briefly introduced. Apparently, the accompanying drawings in the following explanation illustrate merely some embodiments of the present disclosure, and those skilled in the art may obtain other accompanying drawings based on these accompanying drawings without paying any creative effort. It should be noted that the scales shown in the drawings are indicative only and do not represent actual scales.

DETAILED DESCRIPTION

In order to make objects, solutions and advantages of embodiments of the present disclosure clearer, a clear and thorough description for technical solutions in the embodiments of the present disclosure will be given below in conjunction with the accompanying drawings in the embodiments of the present disclosure. Apparently, the described embodiments are a part of embodiments of the present disclosure, not all the embodiments. All other embodiments obtained, based on the embodiments in the present disclosure, by those skilled in the art without paying creative effort fall within the protection scope of the present disclosure.

In the related art, the prognosis of a disease is generally evaluated based on the size of a lesion and the presence or absence of enhancement, which has certain limitations. Taking brain glioma as an example, it originates from neuroglial cells and is the most common tumor of the central nervous system, accounting for approximately 50%~60% of intracranial tumors. The incidence shows a rising trend annually. The World Health Organization classifies gliomas into low (I and II) and high (III and IV) grades. The high-grade glioma (HGG) has a poor prognosis. Grade IV glioblastoma is the most malignant, with a 10-year survival rate of less than 3% and a median survival of about 12 to 14 months. Previous studies have limitations in evaluating the prognosis of glioma by using tumor location, size, resection range, and traditional imaging methods as prognostic predictors.

However, when using multi-factor analysis to evaluate, researchers need to follow up with many patients during diagnosis, treatment, and postoperative processes, collect diagnostic and treatment information, as well as patients' physiological index information, and then analyze and screen image prognostic factors. This work requires significant manpower and material resources. It is time-consuming and labor-intensive, and manually analyzing and screening the prognostic factors alone can take a long time, leading to low efficiency.

In view of this, the present disclosure proposes a method for prognosis evaluation, and the specific concept is as follows. Sample information of multiple modalities is taken as a training sample and trained to obtain a target model, and prognosis evaluation is performed using the target model. The sample information of the multiple modalities includes at least two of an MR sample image, clinical sample information, and gene sample information. Thus, information sources may be enriched so that prognostic factors may be screened from multiple dimensions. In the model training process, parameters of a preset model are updated with a consistency expression value as a factor so that a prognostic factor closely related to a target disease in the information of the multiple modalities may be screened to improve the clinical importance of the prognostic factor, and thus a result output by the target model has a high prognostic reference value.

Figure 1:
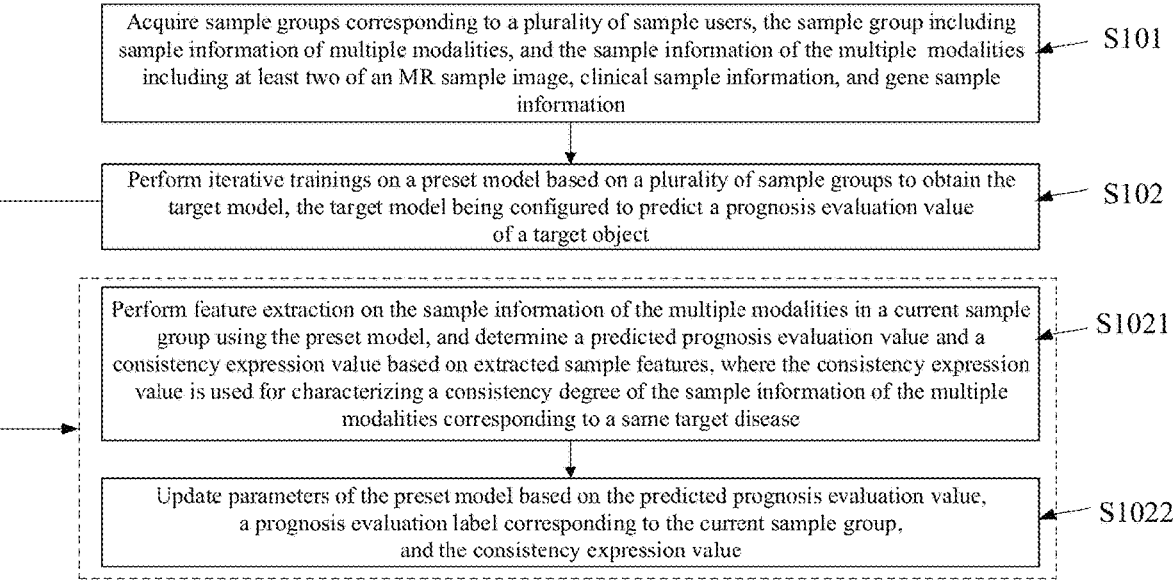
FIG. 1 is a flowchart schematically illustrating steps of a method for acquiring a target model.

Referring to FIG. 1, a flowchart of steps of a method for acquiring a target model of the present disclosure is shown. As shown in FIG. 1, the following steps may be specifically included.

At S101, a plurality sample groups are acquired, the sample groups each correspond to a plurality of sample users. The sample group includes sample information of multiple modalities, and the sample information of the multiple modalities includes at least two of an MR (magnetic resonance) sample image, clinical sample information, and gene sample information.

At S102, a target model is obtained by performing iterative trainings on a preset model based on the plurality of sample groups. The target model is configured to predict a prognosis evaluation value of a target object.

The following steps are performed in each iterative training in S102.

At S1021, a feature extraction is performed on the sample information of the multiple modalities in a current sample group using the preset model, and a predicted prognosis evaluation value and a consistency expression value are determined based on extracted sample features. The consistency expression value is used for characterizing a consistency degree of the sample information of the multiple modalities reflecting a same target disease.

At S1022, parameters of the preset model are updated based on the predicted prognosis evaluation value, a prognosis evaluation label corresponding to the current sample group, and the consistency expression value.

In the embodiment, the sample user may refer to a user who clearly knows the prognostic survival time and quality of life for suffering from a target disease. The target disease may be any clinically known disease, such as intracranial tumor as mentioned above, common hepatobiliary and pulmonary tumors, which is not specifically limited here.

The age and gender of the sample users may be diversified as much as possible. The sample information of the multiple modalities may include at least two of the MR sample image, the clinical sample information, and the gene sample information. The sample information of different modalities may be used for reflecting a characterization in a corresponding dimension after the sample user suffers from the target disease. For example, MR sample information may reflect a morphological characterization of an organ tissue after the sample user suffers from the target disease, the clinical sample information may reflect a characterization of a diagnostic treatment after the sample user suffers from the target disease, and the gene sample information may reflect a characterization of an expression state of certain genes after the sample user suffers from the target disease.

The MR sample image may be used for reflecting a morphological feature of a corresponding organ tissue after the sample user suffers from the target disease. Specifically, the MR sample image may be directly acquired from a magnetic resonance imaging (MRI) device, a memory, or any other suitable source. For example, the MR sample image of the sample user may be acquired from a medical database after obtaining the corresponding authority. It should be noted that the MR sample image is an image related to the target disease of the sample user. For example, if the sample user suffers from a brain glioma, the MR sample image is an MR image of the brain of the sample user, which may reflect morphological features of brain tissues. As another example, if the sample user suffers from a liver tumor, the MR sample image may be an MR image of the abdomen of the user, which may reflect morphological features of abdominal tissues.

The clinical sample information may include information of the sample user during diagnosis and therapy, such as drug information, hospitalization information, therapeutic regimen information, attending physician information, and hospital information.

The gene sample information may include information of genes related to the occurrence and prognosis of the target disease. Specifically, information of each gene in the gene sample information includes a name of the gene and an expression state of the gene, because the onset and prognosis of the disease may be reflected in the expression of some genes. For example, in the case of brain glioma, taking the telomerase reverse tranase (TERT) gene as an example, it is one of the important genes encoding a telomerase complex, the TERT gene has no transcriptional activity in most non-tumor cells, but TERT gene mutation such as promoter mutation, gene translocation, and DNA amplification exists in 73% of tumors. That is, an expression category of the above-mentioned genes has a certain correlation with tumors.

In the embodiment, at least two of the MR sample image, the clinical sample information, and the gene sample information may be taken as a sample group of the sample user. In a specific example, the MR sample image in the sample group may be necessary, namely, any one or both of the clinical sample information and the gene sample information may be combined with the MR sample image to obtain the sample group. Specifically, the sample group may include the MR sample image and the clinical sample information, or may include the MR sample image and the gene sample information, or may include the MR sample image, the clinical sample information, and the gene sample information.

The preset model may be subjected to iterative trainings with a plurality of sample groups as the training samples. Specifically, during each training, a plurality of sample groups may be input into the preset model in batches, or only one sample group is input into the preset model.

In the embodiment, in each iterative training, the feature extraction may be performed on the sample information of the multiple modalities in the current sample group using the preset model. The current sample group refers to a sample group input into the preset model at the current time, and in the case of inputting a plurality of sample groups to the preset model at a time, the current sample group refers to any sample group among the plurality of sample groups input at the current time.

The preset model may be configured to perform a feature extraction on the sample information of each modality in the current sample group to obtain the sample feature corresponding to each sample information. Specifically, for the MR sample image, the extracted feature is a radiomics feature vector. For the clinical sample information, the extracted feature is a feature vector obtained through performing feature vector conversion on the clinical information. For the gene sample information, the extracted feature is a feature vector obtained through performing feature vector conversion on the gene information.

The predicted prognosis evaluation value of the sample object corresponding to the current sample group may be determined according to the sample feature extracted from information of each modality. In a specific implementation, a feature fusion may be performed on the sample features corresponding to information of a plurality of modality, then the predicted prognosis evaluation value is determined based on a fused feature.

In practice, the sample information of different modalities should all contain a description of the target disease, and each should contain a large amount of consistent information about the target disease. However, the sample information of different modalities also contains information unrelated to the target disease. For example, the MR sample image contains images of other normal tissue sites in addition to the lesion sites, and the images of normal tissue sites may not have related information in the sample information of other modalities, for example, this part of information is not contained in the clinical sample information, so the preset model should learn to discard this part of useless information in the training process.

Therefore, in the embodiment, the preset model may determine the consistency expression value based on the sample features corresponding to the information of the plurality of modality, and the consistency expression value is incorporated into the construction of a loss function to update the parameters of the preset model, so that the preset model continuously enhances an expression degree of the extracted sample features on the target disease based on the consistency expression value.

In this way, the consistency expression value may be used for characterizing the consistency degree of the sample features corresponding to the information of the plurality of modality reflecting the target disease, namely, whether the extracted sample features consistently express the target disease.

Illustratively, when the consistency expression value is high, it means that the sample features extracted from the MR sample image, the clinical sample information, and the gene sample information are all features for expressing the target disease. For the MR sample image, the extracted sample features are features for expressing the lesion site of the target disease. For the clinical sample information, the extracted sample features are the expression of the diagnosis and the therapeutic regimen of the target disease, and the expression of the target disease in the patient's age, occupation, etc. For the gene sample information, the extracted sample features are used for characterizing the expression of the target disease on related genes.

The prognosis evaluation label of the present disclosure is a real prognosis condition of the sample object. If the prognostic survival time needs to be predicted, the prognosis evaluation label is a real prognostic survival time of the sample object, and the predicted prognosis evaluation value may be represented as a prognostic age. If the prognostic quality of life needs to be predicted, the prognosis evaluation label is a real prognostic quality of life grade of the sample object, including high grade, low grade, and medium grade, and the predicted prognosis evaluation value may be represented as the prognostic quality of life grade.

By adopting the technical solution of the embodiment, when the parameters of the preset model are updated, the consistency expression value, the predicted prognosis evaluation value, and the prognosis evaluation label are incorporated in the construction of the loss function. Thus, with the training of the model, on the one hand, the expression degree of the extracted sample features on the target disease may be enhanced based on the consistency expression value, so that the prognostic factor for determining the prognosis evaluation value is strongly related to the target disease. Therefore, the clinical importance of the prognostic factor may be improved so that the prognosis evaluation value can be more medically referenced. On the other hand, the parameters of the preset model may be continuously updated based on a difference between the predicted prognosis evaluation value the real situation. Thus, a clinical reference value of the prognosis evaluation value may be further improved.

On another hand, in the present disclosure, the prognosis is predicted using the sample information of the multiple modalities. Thus, the complementarity between the sample information of different modalities may be used as the prognostic factor of the target disease, thereby enriching the data source of the prognostic factors, and improving the medical reference of the prognosis evaluation value.

In an alternative implementation, in the case that the target disease is glioma, the gene sample information may include information of at least one gene of isocitrate dehydrogenase (IDH), a chromosome 1p/19q joint deletion state, a TERT gene promoter, and an O6-methylguanine-DNA methyltransferase (MGMT) promoter methylation; the clinical sample information includes at least one clinical information of gender, age, histological diagnosis, tumor grading, medication information, and history of malignant tumors.

The information of each gene in the gene sample information may include the name of the gene and the expression category of the gene, and the expression category may be different according to different genes. Specifically, the expression categories in the information of the IDH gene are mutant type and wild type. The expression states of the 1p/19q gene include a deleted state and an undeleted state. The expression categories of the MGMT promoter are methylated and unmethylated. The expression categories of the TERT promoter include mutant type and wild type, and the information of various types of genes is specifically shown in the following Table 1.

TABLE 1

| Gene sample information | | | | |
| --- | --- | --- | --- | --- |
| Name | IDH | 1p/19q | TERT | MGMT |
| TCGA-CS-4938 | Mutant | non-codel | WT | Unmethylated |
| TCGA-CS-4941 | WT | non-codel | Mutant | Methylated |

The clinical sample information may include one or more of the gender, age, histological diagnosis, tumor grading, medication information, and history of malignant tumors of the sample object. Of course, in practical situations, the clinical sample information may not only be limited to the above-mentioned clinical information, but also include more clinical information, such as the occupation and region of the sample object, any information related to the occurrence and prognosis of the target disease may be used as the clinical information.

In an example, the clinical sample information may be as shown in Table 2 below.

TABLE 2

| Clinical sample information | | | | | | | |
| --- | --- | --- | --- | --- | --- | --- | --- |
| Name | Age | Gender | Histology | Grade | Drug_name | History_other_malignancy | Survival (months) |
| TCGA-CS-4938 | 31 | female | astrocytoma | G2 | Temodar | No | 4.69 |
| TCGA-CS-4941 | 67 | male | astrocytoma | G3 | None | No | 7.68 | and the prognosis evaluation label. Therefore, the predicted prognosis evaluation value predicted through the model may approach the prognosis evaluation label infinitely with the proceeding of the training, and then the prognosis evaluation value may approach the prognosis evaluation value under In an embodiment, the sample information of the multiple modalities may include the MR sample image, the clinical sample information, and the gene sample information. That is, each sample group includes the MR sample image, the clinical sample information, and the gene sample information. Therefore, the feature extraction is required to be performed on the sample information of three modalities in each iterative training.

In the training process, each iterative training includes stages of feature extraction and constructing the loss function based on the output of the model to update the parameters.

The sample information of each modality may include a plurality of sub-sample information. In the stage of feature extraction, feature extraction may be performed on each sub-sample information in the sample information of each modality. Then, a feature fusion is performed on features of a plurality of sub-sample information in the sample information of one modality to obtain a sample feature corresponding to the sample information of this modality.

Hereinafter, the two stages are described separately.

Stage 1: Stage of Feature Extraction.

As described above, in one implementation, the sample information of each modality includes a plurality of sub-sample information. For the sample information of each modality, feature extraction is performed on a plurality of sub-sample information in the sample information of the modality to obtain corresponding multiple sub-feature vectors. Then, a feature fusion is performed on the multiple sub-feature vectors corresponding to the sample information of each modality to obtain a sample feature corresponding to the sample information of this modality.

For the feature extraction of each sub-sample information, as described in the above-mentioned embodiment, after obtaining the sub-feature vector corresponding to the sub-sample information, a feature fusion may be performed according to the following process to obtain the sample feature.

For the MR sample image, the sub-sample information may be one slice image of the MR sample image, and when feature extraction is performed, feature extraction may be performed on each slice image to obtain sub-feature vectors corresponding to various slice images. Then, the sub-feature vectors corresponding to the slice images are fused to obtain a sample feature of the MR sample image.

For the clinical sample information, the sub-sample information may be a kind of clinical information in the clinical sample information. For example, the age, gender, and tumor grading in the clinical information may all be taken as a piece of sub-sample information. When feature extraction is performed, feature extraction is performed on each kind of information. Specifically, each kind of information is converted into a feature vector to obtain the sub-feature vector corresponding to this kind of information, and then the sub-feature vectors corresponding to various kinds of clinical information in the clinical sample information are fused to obtain a sample feature of the clinical sample information.

For the gene sample information, the sub-sample information may be information of one gene in the gene sample information, such as information of IDH and information of the TERT gene promoter. Then, the information of each gene may be converted into the sub-feature vector, and then the sub-feature vectors corresponding to the information of various genes in the gene sample information are fused to obtain a sample feature of the gene sample information.

In an alternative example, when the sub-feature vectors corresponding to the sample information of each modality are fused, the fusion may be performed directly according to a preset weight corresponding to each sub-feature vector. For example, a preset weight may be manually set for each slice image in advance, a weight may also be set for each kind of clinical information, and a corresponding preset weight may also be set for information of each gene. The preset weight may characterize the importance of this kind of sub-sample information to the prognosis. Thus, feature fusion may be performed based on the importance of each sub-feature vector to obtain features that are important to prognosis evaluation, thereby improving the medical value of prognosis evaluation.

In yet another example, an attention mechanism may be fused in the preset model. For the sample information of each modality, a correlation degree between the sub-feature vectors may be determined through the attention mechanism, and then the sub-feature vectors are fused based on the correlation degree, so that the features with a higher correlation degree in the sample information of the modality may be fused to improve the correlation between the prognostic factors, thereby making the prognostic factors for the prognosis evaluation of the target model closely related, further improving the clinical importance, and making the target model have medical interpretability.

In a specific implementation, an attention value between every two sub-feature vectors may be determined. The plurality of sub-feature vectors are fused based on the attention value to obtain the sample feature corresponding to the sample information of the modality.

As described above, the attention value is used for characterizing a degree of closeness between the two sub-feature vectors.

When the sub-feature vectors are fused based on the attention value between every two sub-feature vectors, in one example, the two sub-feature vectors may be fused based on the attention value between every two sub-feature vectors to obtain a fused vector, thereby obtaining a plurality of fused vectors. Then, the plurality of fused vectors are fused to obtain the sample feature. For example, the sub-feature vectors include a vector i, a vector j, and a vector k, and when being fused, the vector i and the vector j may be fused to obtain a fused vector ij. Similarly, a fused vector ik and a fused vector jk are obtained, and then the fused vector ij, the fused vector ik, and the fused vector jk are fused to obtain the sample feature.

In yet another example, for each sub-feature vector, all the other sub-feature vectors are fused into the sub-feature vector based on attention values between the sub-feature vector and all the other sub-feature vectors to obtain a fused sub-vector for the sub-feature vector. Re-fusion is performed on a plurality of fused sub-vectors to obtain the sample feature corresponding to the sample information of the modality.

Illustratively, the sub-feature vectors include the vector i, the vector j, and the vector k, and when being fused, the vector j and the vector k may be fused into the vector i according to the attention value between the vector i and the vector j and the attention value between the vector i and the vector k to obtain a fused sub-vector i'. Similarly, a fused sub-vector j' and a fused sub-vector k' are obtained, and then the fused sub-vector i', the fused sub-vector j', and the fused sub-vector k' are fused to obtain the sample feature.

For the clinical sample information, the attention value may be determined according to the following process, and feature fusion may be performed based on the attention value.

The attention value between every two sub-feature vectors may be determined based on an average attention value of the plurality of clinical information and the two sub-feature vectors. The average attention value of the plurality of clinical information may be acquired by referring to the following formula (1).

$$S = e^{(va^T \cdot vg)} + e^{(va^T \cdot vh)} + e^{(va^T \cdot vgr)} + e^{(va^T \cdot vd)} + e^{(va^T \cdot vhom)} \qquad \text{Formula (1)}$$

va represents a sub-feature vector corresponding to age, vg represents a sub-feature vector corresponding to gender, vh represents a sub-feature vector corresponding to histological diagnosis, vhom represents a sub-feature vector corresponding to history of malignant tumors, vd represents a sub-feature vector corresponding to medication information, and vgr represents a sub-feature vector corresponding to tumor grading information. S represents the average attention value.

Then, the attention value between every two sub-feature vectors may be determined according to the following formula (2):

$$Si = \frac{e(vi^T \cdot vj)}{S} \qquad \text{Formula (2)}$$

Si represents an attention value between a sub-feature vector vi and a sub-feature vector vj.

Accordingly, when feature fusion is performed, one sub-feature vector may be fused with all the other sub-feature vectors, and then the obtained fused sub-vectors are fused. Specifically, taking the fusion of the sub-feature vector corresponding to the age information in the clinical information as an example, a fused sub-vector corresponding to the age information may be determined according to the following formula (3):

$$va\_att = \frac{e^{(va^T \cdot vg)}}{S} \times vg + \frac{e^{(va^T \cdot vh)}}{S} \times vh + \frac{e^{(va^T \cdot vgr)}}{S} \times \qquad \text{Formula (3)}$$
$$vgr + \frac{e^{(va^T \cdot vd)}}{S} \times vd + \frac{e^{(va^T \cdot vhom)}}{S} \times vhom$$

In formula (3), $va_{att}$ is the fused sub-vector corresponding to the age information.

For the gene sample information, processes of determining the attention value and performing feature fusion based on the attention value may be performed by referring to the above-mentioned clinical sample information, and will not be described in detail herein.

For the MR sample image, the attention value may be determined according to the following process, and feature fusion may be performed based on the attention value.

In an example, in the stages of feature extraction and feature fusion, since it is necessary to extract a prognostic factor of higher clinical importance, namely, to extract a feature vector of higher clinical importance, in the example, parameter matrices may be set for the stages of feature extraction and feature fusion, and the parameter matrix may be continuously updated with the training of the model to extract the prognostic factor of higher importance.

Specifically, as described above, the MR sample image includes a plurality of slice sample images, each slice sample image being a piece of sub-sample information. Specifically, for each slice sample image included in the MR sample image, the attention value between the sub-feature vectors corresponding to every two slice sample images is determined based on a current value of a first parameter matrix. Then, the sub-feature vectors may be fused based on the attention value.

In a specific implementation, the attention value between the sub-feature vectors corresponding to every two slice sample images may be determined according to the following formula (4):

$$\alpha_{i,j} = \frac{e^{(Q \times V_i)^T \cdot (K \times V_j)}}{\sum_j e^{(Q \times V_i)^T \cdot (K \times V_j)}} \qquad \text{Formula (4)}$$

In formula (4), Q and K are the first parameter matrices, where values of Q and K may be different. In practice, Q and K may be a parameter matrix of 512×512. $v_i$ is a sub-feature vector corresponding to an i-th slice sample image. $v_j$ is a sub-feature vector corresponding to a j-th slice sample image. $\alpha_{i,j}$ is an attention value between the i-th slice sample image and the j-th slice sample image.

Then, for each sub-feature vector, all the other sub-feature vectors are fused into the sub-feature vector based on attention values between the sub-feature vector and all the other sub-feature vectors to obtain the fused sub-vector for the sub-feature vector according to the following formula (5):

$$SV_i^1 = \sum_{1=1}^n \alpha_{i,j} V_j^1 \qquad \text{Formula (5)}$$

In formula (5), $$SV_i^1$$

is a fused sub-vector corresponding to the i-th slice sample image, and n represents a total number of the slice sample images.

Later, the fused sub-vectors are fused to obtain the sample feature of the MR sample image according to the following formula (6):

$$SV = \frac{\Sigma_{i=1}^n SV_i}{n} \qquad \text{Formula (6)}$$

SV represents the sample feature of the MR sample image, and $SV_i$ represents the fused sub-vector corresponding to the i-th slice sample image.

In a further embodiment, since the parameter matrices are set for the stages of feature extraction and feature fusion, and the parameter matrix may be continuously updated with the training of the model, the prognostic factor of higher importance is extracted. The clinical sample information and the gene sample information may be further fused based on the set parameter matrix when the sub-feature vectors are fused.

For each piece of clinical sub-sample information in the clinical sample information, feature fusion is performed on sub-feature vectors corresponding to the clinical sub-sample information based on a current value of a second parameter matrix to obtain a sample feature corresponding to the clinical sample information.

For each piece of gene sub-sample information in the gene sample information, feature fusion is performed on sub-feature vectors corresponding to the gene sub-sample information based on a current value of a third parameter matrix to obtain a sample feature corresponding to the gene sample information.

Specifically, after obtaining each fused sub-vector corresponding to the sub-feature vector from the above-mentioned formula (3), feature fusion may be performed on fused sub-vectors corresponding to the sub-feature vectors corresponding to the clinical sub-sample information based on the current value of the second parameter matrix to obtain the sample feature corresponding to the clinical sample information. Specifically, fusion may be performed according to the following formula (7) and formula (8):

$$CV = \frac{vp^T \cdot va\_att}{S_1} \times va\_att + \frac{vp^T \cdot vg\_att}{S_1} \times vg\_att + \qquad \text{Formula (7)}$$

$$\frac{vp^T \cdot vh\_att}{S_1} \times vh\_att + \frac{vp^T \cdot vgr\_att}{S_1} \times vgr\_att +$$

$$\frac{vp^T \cdot vd\_att}{S_1} \times vd\_att + \frac{vp^T \cdot vhom\_att}{S_1} \times vhom\_att;$$

$$S_1 = \qquad \text{Formula (8)}$$

$$vp^T \cdot (ya\_att + yg\_att + vh\_att + vgr\_att + vd\_att + vhom\_att);$$

CV represents the sample feature corresponding to the clinical sample information, and vp is the second parameter matrix, which may be a parameter vector of 128×1.

The fusion of fused sub-vectors corresponding to the gene sub-sample information may also be performed by referring to the above-mentioned formula (7) and formula (8). The second parameter matrix and the third parameter matrix may both be parameter vectors of 128×1, and parameters in the second parameter matrix and the third parameter matrix are updated with the update of the preset model (that is, they are updated according to a loss value of the loss function).

In a further example, the clinical sample information includes numerical sub-sample information and non-numerical sub-sample information. In the stage of feature extraction, based on a parameter set that is set for the above-mentioned preset model, the numerical sub-sample information is mapped to a vector space according to the parameter set for the model, and parameters in the parameter set are continuously updated during the training process, so that numerical clinical information of different sample objects may be mapped within a spatial range, and then a comprehensive prognostic factor of the numerical clinical information may be extracted. For example, for different patients of the same age, the parameters in the parameter set are updated after a sample group of a patient A is input into the preset model for training. Later, when a sample group of a patient B is input into the preset model for training, vector mapping is performed on the age based on the updated parameters in the parameter set. Therefore, in the training process, the feature vectors corresponding to different patients of the same age may be different, but change within a certain spatial range. Thus, the influence of age group on the prognosis may be obtained in the prognosis evaluation.

In a specific implementation, for the clinical sample information, in each iterative training, for the clinical sample information in the current sample group, the non-numerical sub-sample information is converted into a first sub-feature vector. Moreover, the numerical sub-sample information is mapped to a target space based on a current value of each parameter in the parameter set to obtain a corresponding second sub-feature vector. The first sub-feature vector and the second sub-feature vector are fused to obtain the sample feature corresponding to the clinical sample information.

In the embodiment, the parameters in the parameter set are used for determining a dimension of the target space and a value at each spatial point.

The non-numerical sub-sample information may refer to sub-sample information in a character string format or sub-sample information of a literal type. For example, the gender "male" is the sub-sample information of the literal type, and the tumor grading is the sub-sample information of the character string type. For the non-numerical sub-sample information, the feature vectors corresponding to the sub-sample information may be preset in advance. Then, for the clinical sample information in the current sample group, the first sub-feature vector corresponding to the non-numerical sub-sample information in the current sample group may be obtained by looking up a table. The table includes feature vectors corresponding to various non-numerical sub-sample information, which may be understood as a fixed feature vector.

The numerical sub-sample information may be sub-sample information of a numerical type. For example, the age "62" is the sub-sample information of the numerical type. For this type of sub-sample information, the numerical sub-sample information may be mapped to the target space based on the current values of the parameters in the parameter set. The target space may be a vector space, and the vector space may be a two-dimensional space, including a plurality of values in a first dimension and a plurality of values in a second dimension on the two-dimensional space. That is, a numerical value may be distributed to various positions in the target space to obtain a second sub-feature vector corresponding to the numerical value.

In this way, parameters in the parameter set may be understood to be weight values that distribute a numerical value to various positions in the target space.

The process of fusing the first sub-feature vector and the second sub-feature vector to obtain the sample feature corresponding to the clinical sample information may be described by referring to the above-mentioned example. For example, the first sub-feature vector and the second sub-feature vector together constitute a plurality of sub-feature vectors, which may be fused according to the above-mentioned fusion method for the plurality of sub-feature vectors.

Specifically, the parameter set includes a first parameter vector, a second parameter vector, and a fourth parameter matrix, and when the numerical sub-sample information is mapped to the target space based on the current value of each parameter in the parameter set to obtain the corresponding second sub-feature vector, the numerical sub-sample information is mapped to a first dimension in the target space based on a current value of the first parameter vector to obtain a mapping value of the first dimension. The second sub-feature vector is determined based on the mapping value of the first dimension, a current value of the second parameter vector, and a current value of the fourth parameter matrix.

The first parameter vector is used for determining a value of a spatial point of the target space in the first dimension. The second parameter vector is used for determining a value of a spatial point of the target space in a second dimension. The fourth parameter matrix is used for assigning a parameter to each spatial position in the first dimension and the second dimension.

The first parameter vector may be understood to be a weight value that distributes a numerical value to various positions in the first dimension of the target space. The second parameter vector may be understood to be a weight value that distributes a numerical value to various positions in the second dimension of the target space. The fourth parameter matrix may be understood to be a weight value that distributes a numerical value to each position in the target space.

Specifically, the numerical sub-sample information may be mapped to the first dimension in the target space based on the current value of the first parameter vector to obtain the mapping value of the first dimension according to the following formula (9):

$$\text{temp\_a} = \text{sigmoid}(w \times a) \qquad \text{Formula (9)}$$

In formula (9), w is the first parameter vector, which in practice may be the parameter vector of the 128× 1 dimension. a is the numerical sub-sample information, for example, a is an age value "62".

Then, the second sub-feature vector may be determined based on the mapping value of the first dimension, the current value of the second parameter vector, and the current value of the fourth parameter matrix according to the following equation (10):

$$sa = W \times \text{temp\_a} + b \qquad \text{Formula (10)}$$

In formula (10), b is the second parameter vector, which in practice may be the parameter vector of the 128×1 dimension. W is the fourth parameter matrix, which in practice may be a parameter matrix of 128. Sa is the second sub-feature vector.

Of course, in yet another embodiment, the parameter set further includes a plurality of third parameter vectors. After determining the second sub-feature vector, the second sub-feature vector may also be modified specifically according to the following formula (11):

$$va = \frac{e^{(sa^T \cdot a_1)}}{\sum_{i=1}^{3} e^{(sa^T \cdot a_i)}} \times a_1 + \frac{e^{(sa^T \cdot a_2)}}{\sum_{i=1}^{3} e^{(sa^T \cdot a_i)}} \times a_2 + \frac{e^{(sa^T \cdot a_3)}}{\sum_{i=1}^{3} e^{(sa^T \cdot a_i)}} \times a_3 \qquad \text{Formula (11)}$$

va is a corrected second sub-feature vector, sa is the second sub-feature vector, and $a_1$, $a_2$, and $a_3$ are the third parameter vectors. Specifically, these three third parameter vectors may all be parameter vectors of 128*1, where differences are allowed between these three third parameter vectors.

Accordingly, the first sub-feature vector and the corrected second sub-feature vector may be fused to obtain the sample feature corresponding to the clinical sample information.

In an alternative example, when the sample features corresponding to the sample information of the multiple modalities are fused, the sample features may be mapped to the same space and then fused. Specifically, the parameters of the preset model include a dimension parameter matrix corresponding to the sample information of each modality. In this way, dimension transformation may be performed on the sample feature corresponding to the sample information of each modality based on the sample feature and the dimension parameter matrix corresponding to the sample information of the modality to obtain a converted sample feature. The predicted prognosis evaluation value and the consistency expression value are determined based on the converted sample feature corresponding to each piece of the sample information of the multiple modalities.

Each dimension parameter matrix is used for adjusting the dimension of the sample feature corresponding to the sample information of the modality. Specifically, dimension adjustment may be performed on the sample feature corresponding to the sample information of the modality according to the following formulas (12) to (14):

$$PV_1 = M_1 \cdot SV \qquad \text{Formula (12)}$$

$$PV_2 = M_2 \cdot CV \qquad \text{Formula (13)}$$

$$PV_3 = M_3 \cdot GV \qquad \text{Formula (14)}$$

$PV_1$ is a converted sample feature corresponding to the MR sample image, $PV_2$ is a converted sample feature corresponding to the clinical sample information, and $PV_3$ is a converted sample feature corresponding to the gene sample information.

SV is the sample feature corresponding to the MR sample image, CV is the sample feature corresponding to the clinical sample information, and GV is the sample feature corresponding to the gene sample information.

$M_1$ is a dimension parameter matrix corresponding to the MR sample image, which may be a parameter matrix of 64×512. $M_2$ is a dimension parameter matrix corresponding to the clinical sample information, which may be a parameter matrix of 64×128. $M_3$ is a dimension parameter matrix corresponding to the gene sample information, which may be the parameter matrix of 64× 128.

Stage 2: Stage of Updating Parameters.

In the present disclosure, it is necessary to update the parameters of the preset model based on the predicted prognosis evaluation value, the prognosis evaluation label corresponding to the current sample group, and the consistency expression value. In a specific implementation, the difference between the predicted prognosis evaluation value and the prognosis evaluation label may be acquired. The parameters of the preset model are updated with a target of minimizing the difference and maximizing the consistency expression value.

The difference between the predicted prognosis evaluation value and the prognosis evaluation label may reflect a distance between the prognosis evaluation value predicted through the preset model and a real prognosis evaluation value. The consistency expression value may characterize the consistency degree of the sample features corresponding to the same target disease. In the training process, the training target may be minimizing the difference between the predicted prognosis evaluation value and the prognosis evaluation label and maximizing the consistency expression value.

In this way, the parameters of the preset model may be updated with the target of minimizing the difference and maximizing the consistency expression value.

In a specific implementation, when updating the parameters of the preset model with the target of minimizing the difference and maximizing the consistency expression value, a loss function as shown in the following formula (15) may be constructed based on the difference and the consistency expression value:

$$loss = \sum_i (y_i' - y_i)^2 - consistency \qquad \text{Formula (15)}$$

The parameters of the preset model are updated based on a loss value of the loss function with the target of minimizing the difference and maximizing the consistency expression value. The loss represents the loss value, $$y_i'$$

represents the predicted prognosis evaluation value, $y_i$ represents the prognosis evaluation label, and consistency represents the consistency expression value.

As can be seen from the above-mentioned loss function, the training target is to minimize the loss value, then in order that the loss value may be minimized, it is necessary to minimize the difference and maximize the consistency expression value. It is noted that the consistency expression value of the present disclosure may be a numerical value between 0 and 1.

In an example, the consistency expression value may be determined as follows.

Firstly, each of the sample features is transposed to obtain a transposed feature corresponding to each of the sample features. Then, for two different sample features, one of the two sample features is fused with the transposed feature corresponding to the other sample feature to obtain a corresponding fused feature value. The consistency expression value is determined based on each fused feature value.

In an embodiment, the transposed feature corresponding to each of the sample features may be determined based on the following formula (16):

$$PV^T \cdot PV = 1 \qquad \text{Formula (16)}$$

In formula (16), PV is the sample feature, $PV^T$ is the transposed feature, and a result of dot product between the two is 1. That is, the sample features may be normalized by transposing.

Then, one of the two sample features is fused with the transposed feature corresponding to the other sample feature to obtain the corresponding fused feature value according to the following formula (17):

$$PV12 = PV_1^T \cdot PV_2 \qquad \text{Formula (17)}$$

In formula (18), $$PV_1^T$$

is a transposed feature of a sample feature 1, and $PV_2$ is a sample feature 2, and a result of dot product between the two is between 0 and 1.

Taking the sample information including the MR sample information, the clinical sample information, and the gene sample information as an example, the consistency expression value may be determined according to formula (18):

$$consistency = PV_1^T \cdot PV_2 + PV_2^T \cdot PV_3 + PV_3^T. \qquad \text{Formula (18)}$$

$PV_1$ is the sample feature of the MR sample image, $PV_2$ is the sample feature of the clinical sample information, and $PV_3$ is the sample feature of the gene sample information.

$$PV_1^T$$

is a transposed feature corresponding to the sample feature of the MR sample image, $$PV_2^T$$

is a transposed feature corresponding to the sample feature of the clinical sample information, and $$PV_3^C$$

is a transposed feature corresponding to the sample feature of the gene sample information.

Figure 2:
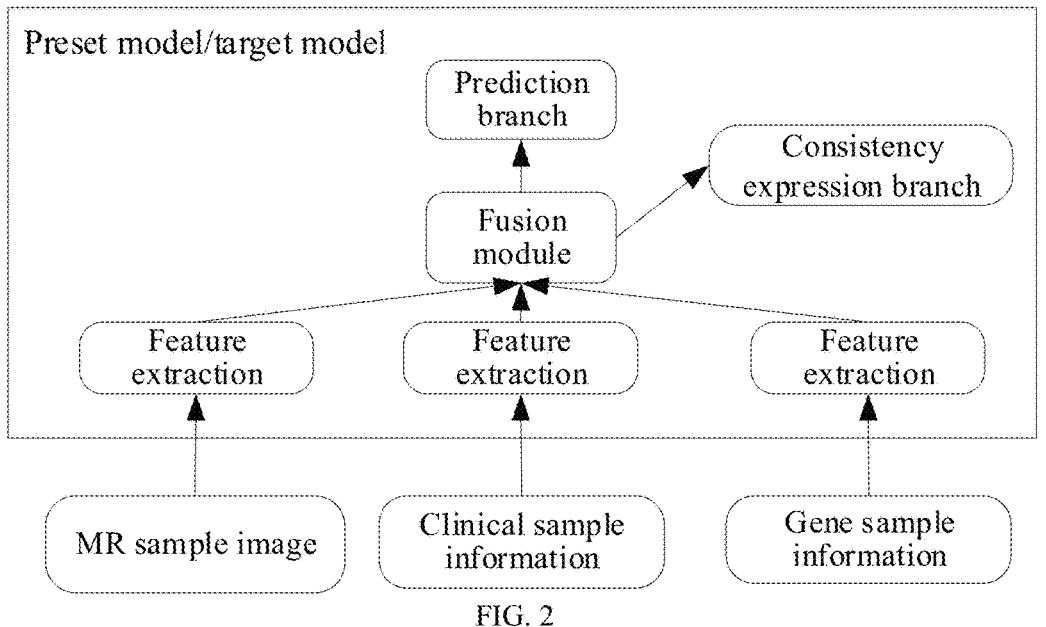
FIG. 2 is a schematic structural diagram of a preset model.

Referring to FIG. 2, a schematic structural diagram of a preset model of the present disclosure is shown. As shown in FIG. 2, the preset model may include a fusion module, a prediction branch, a consistency expression branch, and a data processing module corresponding to the sample information of each modality.

When performing feature extraction on the sample information of the multiple modalities in the current sample group using the preset model, and determining the predicted prognosis evaluation value and the consistency expression value based on the extracted sample features, for the sample information of each modality in the current sample group, feature extraction is performed on corresponding sample information using the data processing module corresponding to the sample information of the modality. Sample features output by the data processing modules are fused using the fusion module. Later, a predicted prognosis evaluation value corresponding to a feature output by the fusion module is determined using the prediction branch. Then, the consistency expression value corresponding to the sample features output by the data processing modules is determined using the consistency expression branch.

That is, the sample information of each modality of the present disclosure is input into a corresponding data processing module, and the sample information of the modality is subjected to feature extraction by the corresponding data processing module. Later, the extracted sample features are input into the fusion module and fused by the fusion module. Then, a fused sample feature is input into a prediction module, and the prediction module determines the predicted prognosis evaluation value based on the fused sample feature.

Hereinafter, the method for acquiring a target model of the present disclosure is exemplarily illustrated in conjunction with the preset model shown in FIG. 2.

At S1, training samples are prepared. The training samples include sample groups corresponding to a plurality of sample users, and each sample group includes the MR sample image, the clinical sample information, and the gene sample information of the sample user.

At S2, the sample groups are input into the preset model. The MR sample image in the sample group is input into an image data processing module, the clinical sample information is input into a clinical data processing module, and the gene sample information is input into a gene data processing module to perform feature extraction of the sample information of the multiple modalities and obtain the sample feature corresponding to the sample information of each modality.

Specifically, the image data processing module is configured to perform feature extraction on a plurality of slice sub-sample images in the MR sample image. After the extraction, feature fusion is performed on sub-feature vectors corresponding to the slice sub-sample images to obtain the sample feature corresponding to the MR sample image.

Figure 3:
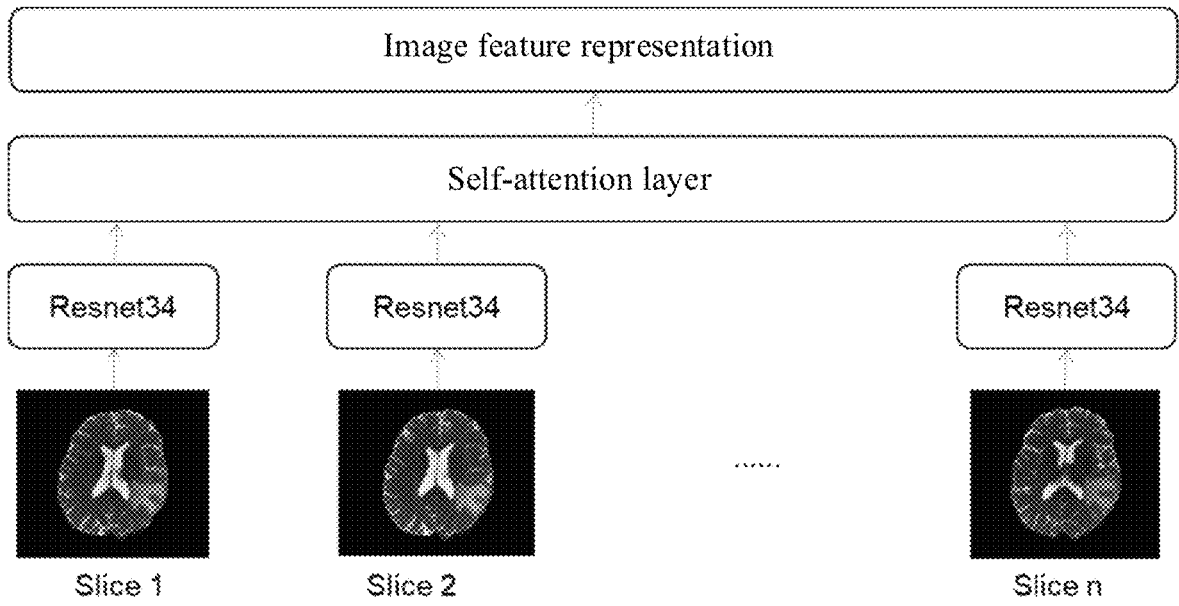
FIG. 3 is a schematic structural diagram of an image data processing module of the present disclosure.
Figure 4:
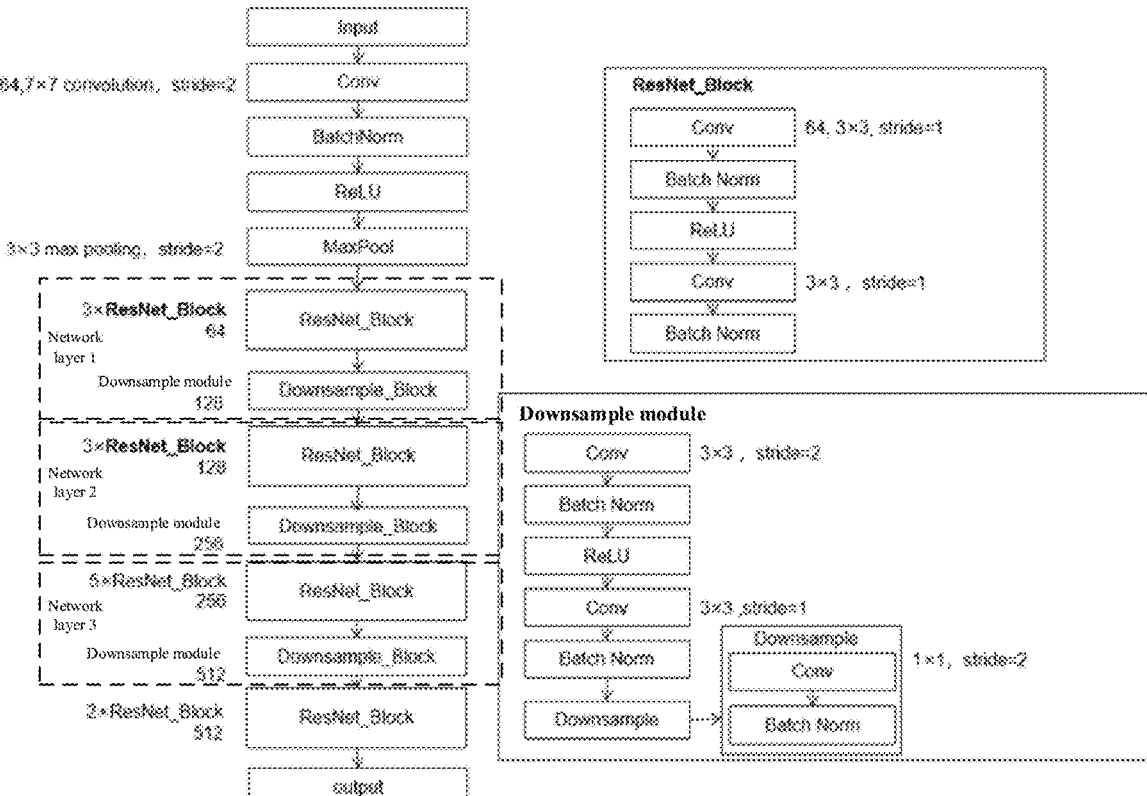
FIG. 4 is a schematic structural diagram of a ResNet network in FIG. 3.

Referring to FIG. 3 and FIG. 4, FIG. 3 is a schematic structural diagram of the image data processing module, and FIG. 4 is a schematic structural diagram of a ResNet network in FIG. 3.

As shown in FIG. 3, a plurality of slice sample images are included, for example Slice1 to Slice n. Each slice sample image is input into a corresponding ResNet network, and feature extraction is performed on the slice sample image through the ResNet network.

As shown in FIG. 4, each input slice sample image in the example has a size of 256×256, and is firstly subjected to a convolution kernel of 7*7 with a stride of 2 and a maximum pooling of 3*3 with a stride of 2, so that the input slice image of 256*256 is converted into a feature map with a size of 64*64, which effectively reduces the size required for storage, and then successively enters a plurality of ResNet_Block and downsample modules. Specifically, the feature map successively enters a network layer 1 composed of three ResNet_Block and a downsample module, a network layer 2 composed of three ResNet_Block and one downsample module, a network layer 3 composed of five ResNet_Block and one downsample module, and a network layer 4 composed of two ResNet_Block, and then enters an average pooling layer to finally output the sub-feature vector of each slice sample image. The sub-feature vector may be a vector of 512×1.

Next, the sub-feature vectors enter a self-attention layer, and the attention value between every two sub-feature vectors is determined by the self-attention layer. Then, the attention value between every two sub-feature vectors is input into a feature representation layer, and the sample feature corresponding to the MR sample image is obtained, based on the attention value, by the feature representation layer according to the above-mentioned formula (4) and formula (5).

As shown in FIG. 4, as shown on the right side, each ResNet_Block successively includes a 3×3 convolution with a stride of 1, Batch Norm regularization, a ReLU activation function, a 3×3 convolution with a stride of 1, and Batch Norm regularization. A structure of the downsample module is similar to ResNet_Block, and includes a 3×3 convolution with a stride of 2, Batch Norm regularization, a ReLU activation function, a 3×3 convolution with a stride of 1, Batch Norm regularization, and downsample (including a 1×1 convolution with a stride of 2 and Batch Norm regularization).

Specifically, the clinical data processing module is configured to perform feature conversion on a plurality of clinical information in the clinical sample information to obtain the sample feature corresponding to the clinical sample information.

In the example, the gender, age, histological diagnosis, tumor grading, medication information, and history of malignant tumors are used as the clinical sample information, and then mapped into the sub-feature vectors. For the sub-sample information of a character type such as gender, histological diagnosis, tumor grading, medication information, and history of malignant tumors, vg, vh, vgr, vd, and vhom may be used to represent the sub-feature vector. Specifically, vector mapping of the sub-sample information of the character type may be completed using a table lookup method.

Finally, the sub-feature vectors are fused using formula (7) to obtain the sample feature corresponding to the clinical sample information.

However, for the numerical sub-sample information such as age, the sub-feature vector corresponding to the numerical sub-sample information may be obtained according to formula (9), formula (10), and formula (11).

Specifically, the gene data processing module is configured to perform feature conversion on information of a plurality of genes in the gene sample information to obtain the sample feature corresponding to the gene sample information.

Similar to the sub-sample information of the character in the clinical sample information, vector mapping of the information of each gene may be completed using the table lookup method to obtain the sub-feature vector corresponding to the information of each gene. Then, the sub-feature vectors are fused using the formula (7) to obtain the sample feature corresponding to the gene sample information.

At S3, the sample features corresponding to the sample information of the multiple modalities are input into the fusion module. The fusion module may fuse the sample features using the formulas (12) to (14), and obtain the consistency expression value corresponding to the sample group currently input into the preset model based on the formulas (16) to (18).

At S4, the fused sample feature output by the fusion module is input into the prediction module, and the prediction module determines the predicted prognosis evaluation value based on the fused sample feature.

At S5, the loss function shown in formula (15) is constructed based on the consistency expression value output by the fusion module, the predicted prognosis evaluation value output by the prediction module, and the prognosis evaluation label corresponding to the sample group currently input into the preset model, and the parameters of the preset model are updated with the target of minimizing the difference and maximizing the consistency expression value.

When the parameters of the preset model are updated, the above-mentioned first parameter matrix, second parameter matrix, third parameter matrix, and fourth parameter matrix as well as the first parameter vector, second parameter vector, and three third parameter vectors in the parameter set may be updated synchronously, so that the accuracy of the data processing modules of the three modalities, the fusion module, and the prediction module may be affected simultaneously in one training based on two optimization targets.

At S6, after the preset model is updated for multiple times, or in the case where the difference between the predicted prognosis evaluation value and the prognosis evaluation label is less than a preset difference and the consistency expression value is greater than or equal to a preset expression value, the training is stopped. The preset model when the training is stopped is taken as the target model, through which the patient's prognosis evaluation value may be predicted.

Figure 5:
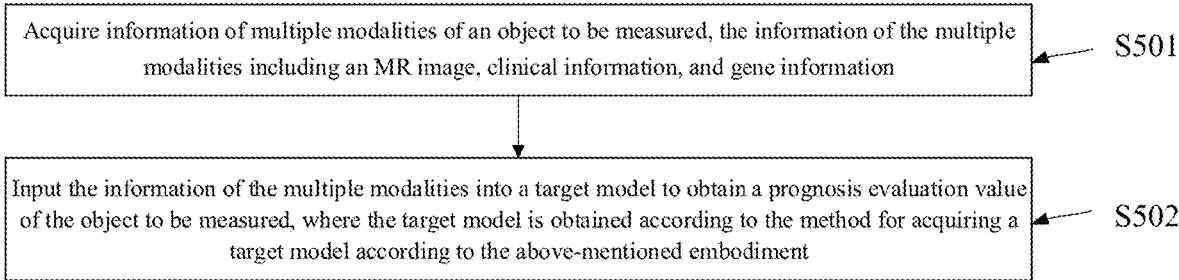
FIG. 5 is a flowchart schematically illustrating steps of a method for determining a prognosis evaluation value.

Accordingly, referring to FIG. 5, a flowchart of steps of a method for determining a prognosis evaluation value of the present disclosure is shown. As shown in FIG. 5, the following steps may be specifically included.

At S501, information of multiple modalities of an object to be measured is acquired, the information of the multiple modalities includes an MR image, clinical information, and gene information.

At S502, the information of the multiple modalities is input into the target model to obtain a prognosis evaluation value of the object to be measured, the target model being obtained by the method for acquiring a target model described in the above-mentioned embodiment.

In the embodiment, after the target model is obtained, the patient's prognosis evaluation value may be predicted using the target model. Then, in practice, the information of the multiple modalities of the object to be measured may be acquired, and the information of the multiple modalities of the object to be measured may be consistent with the modality used for training the preset model. For example, the sample group used for training the preset model includes the MR sample image, the clinical sample information, and the gene sample information, and then the information of the multiple modalities of the object to be measured may also include the MR image, the clinical information, and the gene information of the object to be measured.

In the training process of the target model, the consistency expression value is used as a basis for updating the parameters of the preset model. The consistency expression value is used for characterizing the consistency degree of the sample features corresponding to the same target disease. Thus, with the advancement of training, the preset model may extract the prognostic factors (sample features) related to the target disease, and gradually discard the prognostic factors unrelated to the target disease in the information of each modality. Therefore, the prognostic factors selected by the model are clinically important, which may help to improve the interpretability of the model so that the result output by the target model has a high prognostic reference value.

Of course, in some alternative examples, the target model includes the data processing modules corresponding to the sample information of various modalities and the fusion module connected to the plurality of data processing modules, and the data processing module and the fusion module extract the sample feature strongly related to the expression of the target disease from the sample information of the multiple modalities. Therefore, in an application, after the target model is obtained, the data processing modules and the fusion module in the target model may be extracted separately as a feature extraction model. The feature extraction model may be configured to extract features strongly related to the target disease from the information of the multiple modalities and thus may be independently applied to the screening of the prognostic factors in the prognostic process.

The technical solutions of the embodiments of the present disclosure have the following advantages.

Firstly, through the consistency expression value, the information of different modalities may be mapped to the space reflecting important expression information of the target disease, so that the features extracted from the information of different modalities are closer in the space. Therefore, the complementarity of the information of different modalities may be improved, the influence of noise (non-important information) may be reduced, and the clinical importance thereof to the target disease is reduced, so that the target model has medical interpretability, and the predicted prognosis evaluation value has a higher medical reference value.

Secondly, the information of different modalities may be complementary, which enriches the data source of the prognostic factors and interprets the expression of the target disease from a plurality of dimensions, thus further improving the medical reference of the prognosis evaluation value.

Thirdly, the information within the same modality is combined through a self-attention mechanism, thereby enhancing the non-linear representation capability of the target model.

Fourthly, there is no need for the user to manually screen the prognostic factors multiple times, which improves the efficiency of determining the prognostic factors and reduces the manpower cost.

Figure 6:
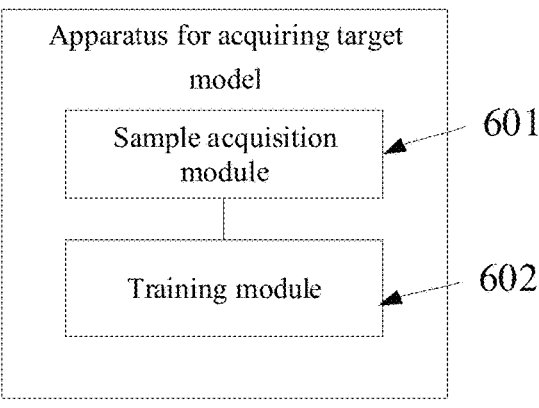
FIG. 6 is a schematic structural diagram of an apparatus for acquiring a target model.

Based on the same inventive concept, the present disclosure also provides an apparatus for acquiring a target model. Referring to FIG. 6, a schematic structural diagram of the apparatus for acquiring a target model is shown. As shown in FIG. 6, the apparatus may specifically include the following modules:

a sample acquisition module 601, configured to acquire sample groups corresponding to a plurality of sample users, each of the sample group includes sample information of multiple modalities, and the sample information of the multiple modalities includes at least two of the MR sample image, the clinical sample information, and the gene sample information; and a training module 602, configured to perform iterative trainings on the preset model based on the plurality of sample groups to obtain a target model, the target model being configured to predict the prognosis evaluation value of the target object, where the following steps are performed in each iterative training.

Feature extraction is performed on the sample information of the multiple modalities in the current sample group using the preset model, and a predicted prognosis evaluation value and a consistency expression value are determined based on the extracted sample features. The consistency expression value is used for characterizing the consistency degree of the sample features corresponding to the same target disease.

The parameters of the preset model are updated based on the predicted prognosis evaluation value, the prognosis evaluation label corresponding to the current sample group, and the consistency expression value.

Optionally, the training module 602 includes a parameter updating unit, and the parameter updating unit includes:

a difference determination subunit, configured to acquire the difference between the predicted prognosis evaluation value and the prognosis evaluation label; and a parameter updating subunit, configured to update the parameters of the preset model with the target of minimizing the difference and maximizing the consistency expression value.

Optionally, the parameter updating subunit is specifically configured to:

construct the following loss function based on the difference and the consistency expression value:

$$\text{loss} = \sum_i (y'_i - y_i)^2 - \text{consistency};$$

update the parameters of the preset model based on the loss value of the loss function with the target of minimizing the difference and maximizing the consistency expression value.

The loss represents the loss value, $y'_i$ represents the predicted prognosis evaluation value, $y_i$ represents the prognosis evaluation label, and consistency represents the consistency expression value.

Optionally, the step of determining the consistency expression value based on the extracted sample features includes the following steps.

Each of the sample features is transposed to obtain a transposed feature corresponding to each of the sample features.

For two different sample features, one of the two sample features is fused with the transposed feature corresponding to the other sample feature to obtain the corresponding fused feature value.

The consistency expression value is determined based on each fused feature value.

Optionally, the sample information of each modality includes the plurality of sub-sample information, and the performing feature extraction on the sample information of the multiple modalities in the current sample group using the preset model includes the following steps.

For the sample information of each modality, feature extraction is performed on the plurality of sub-sample information in the sample information of the modality to obtain the corresponding plurality of sub-feature vectors.

Feature fusion is performed on the plurality of sub-feature vectors corresponding to the sample information of each modality to obtain the sample feature corresponding to the sample information of the modality.

Optionally, the step of performing feature fusion on the plurality of sub-feature vectors corresponding to the sample information of each modality to obtain the sample feature corresponding to the sample information of the modality includes the following steps.

The attention value between every two sub-feature vectors is determined, the attention value being used for characterizing the degree of closeness between the two sub-feature vectors.

The plurality of sub-feature vectors are fused based on the attention value to obtain the sample feature corresponding to the sample information of the modality.

Optionally, the step of fusing the plurality of sub-feature vectors based on the attention value to obtain the sample feature corresponding to the sample information of the modality includes the following steps.

For each sub-feature vector, all the other sub-feature vectors are fused into the sub-feature vector based on attention values between the sub-feature vector and all the other sub-feature vectors to obtain the fused sub-vector for the sub-feature vector.

Re-fusion is performed on the plurality of fused sub-vectors to obtain the sample feature corresponding to the sample information of the modality.

Optionally, the parameters of the preset model include the first parameter matrix, the MR sample image includes the plurality of slice sample images, and the step of determining the attention value between every two sub-feature vectors includes the following steps.

For each slice sample image included in the MR sample image, the attention value between the sub-feature vectors corresponding to every two slice sample images is determined based on the current value of the first parameter matrix.

Optionally, the parameters of the preset model include the second parameter matrix and the third parameter matrix, and the step of performing feature fusion on the plurality of sub-feature vectors corresponding to the sample information of each modality to obtain the sample feature corresponding to the sample information of the modality includes the following steps.

For each piece of clinical sub-sample information in the clinical sample information, feature fusion is performed on the sub-feature vectors corresponding to the clinical sub-sample information based on the current value of the second parameter matrix to obtain the sample feature corresponding to the clinical sample information.

For each piece of gene sub-sample information in the gene sample information, feature fusion is performed on the sub-feature vectors corresponding to the gene sub-sample information based on the current value of the third parameter matrix to obtain the sample feature corresponding to the gene sample information.

Optionally, the parameters of the preset model include the parameter set corresponding to the clinical sample information, the clinical sample information includes the numerical sub-sample information and the non-numerical sub-sample information, and the step of performing feature extraction on the sample information of the multiple modalities in the current sample group using the preset model includes the following steps.

For the clinical sample information in the current sample group, the non-numerical sub-sample information is converted into the first sub-feature vector.

The numerical sub-sample information is mapped to the target space based on the current value of each parameter in the parameter set to obtain the corresponding second sub-feature vector, the parameters in the parameter set being used for determining the dimension of the target space and the value at each spatial point.

The first sub-feature vector and the second sub-feature vector are fused to obtain the sample feature corresponding to the clinical sample information.

Optionally, the parameter set includes the first parameter vector, the second parameter vector, and the fourth parameter matrix, and the step of mapping the numerical sub-sample information to the target space based on the current value of each parameter in the parameter set to obtain the corresponding second sub-feature vector includes the following steps.

The numerical sub-sample information is mapped to the first dimension in the target space based on the current value of the first parameter vector to obtain the mapping value of the first dimension, where the first parameter vector is used for determining the value of the spatial point of the target space in the first dimension.

The second sub-feature vector is determined based on the mapping value of the first dimension, the current value of the second parameter vector, and the current value of the fourth parameter matrix, where the second parameter vector is used for determining the value of the spatial point of the target space in the second dimension, and the fourth parameter matrix is used for assigning a parameter to each spatial position in the first dimension and the second dimension.

Optionally, the parameter set further includes a plurality of third parameter vectors, and the apparatus further includes:

a modification module, configured to correct the second sub-feature vector according to the formula as follows based on the second sub-feature vector and the plurality of third parameter vectors:

$$va = \frac{e^{(sa^T \cdot a_1)}}{\sum_{i=1}^{3} e^{(sa^T \cdot a_i)}} \times a_1 + \frac{e^{(sa^T \cdot a_2)}}{\sum_{i=1}^{3} e^{(sa^T \cdot a_i)}} \times a_2 + \frac{e^{(sa^T \cdot a_3)}}{\sum_{i=1}^{3} e^{(sa^T \cdot a_i)}} \times a_3.$$

va is the corrected second sub-feature vector, sa is the second sub-feature vector, and $a_1$, $a_2$, and $a_3$ are the third parameter vectors.

The step of fusing the first sub-feature vector and the second sub-feature vector to obtain the sample feature corresponding to the clinical sample information includes the following steps.

The first sub-feature vector and the corrected second sub-feature vector are fused to obtain the sample feature corresponding to the clinical sample information.

Optionally, the parameters of the preset model include the dimension parameter matrix corresponding to the sample information of each modality, and the step of determining the predicted prognosis evaluation value and the consistency expression value based on the extracted sample features includes the following steps.

Dimension transformation is performed on the sample feature corresponding to the sample information of each modality based on the sample feature and the dimension parameter matrix corresponding to the sample information of the modality to obtain the converted sample feature.

The predicted prognosis evaluation value and the consistency expression value are determined based on the converted sample feature corresponding to each piece of the sample information of the multiple modalities.

Optionally, the preset model includes the fusion module, the prediction branch, the consistency expression branch, and the data processing module corresponding to the sample information of each modality, and the step of performing feature extraction on the sample information of the multiple modalities in the current sample group using the preset model, and determining the predicted prognosis evaluation value and the consistency expression value based on the extracted sample features includes the following steps.

For the sample information of each modality in the current sample group, feature extraction is performed on corresponding sample information using the data processing module corresponding to the sample information of the modality.

Sample features output by the data processing modules are fused using the fusion module.

The predicted prognosis evaluation value corresponding to the feature output by the fusion module is determined using the prediction branch.

The consistency expression value corresponding to the sample features output by the data processing modules is determined using the consistency expression branch.

Optionally, the gene sample information includes information of at least one gene of IDH, the chromosome 1p/19q joint deletion state, the TERT gene promoter, and the MGMT promoter methylation.

The clinical sample information includes at least one clinical information of the gender, age, histological diagnosis, tumor grading, medication information, and history of malignant tumors.

Figure 7:
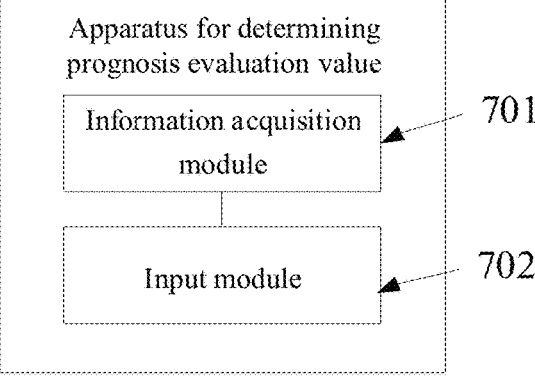
FIG. 7 is a schematic structural diagram of an apparatus for determining a prognosis evaluation value.

Referring to FIG. 7, a schematic structural diagram of an apparatus for determining a prognosis evaluation value is shown. As shown in FIG. 7, the apparatus includes:

an information acquisition module 701, configured to acquire the information of the multiple modalities of the object to be measured, the information of the multiple modalities including the MR image, the clinical information, and the gene information; and an input module 702, configured to input the information of the multiple modalities into the target model to obtain the prognosis evaluation value of the object to be measured, the target model being obtained according to the method for acquiring a target model.

Based on the same inventive concept, the present disclosure also provides an electronic device, including a memory, a processor, and a computer program stored on the memory and executable on the processor, the processor when executed implements the method for acquiring a target model, or when executed implements the method for determining a prognosis evaluation value.

Figure 8:
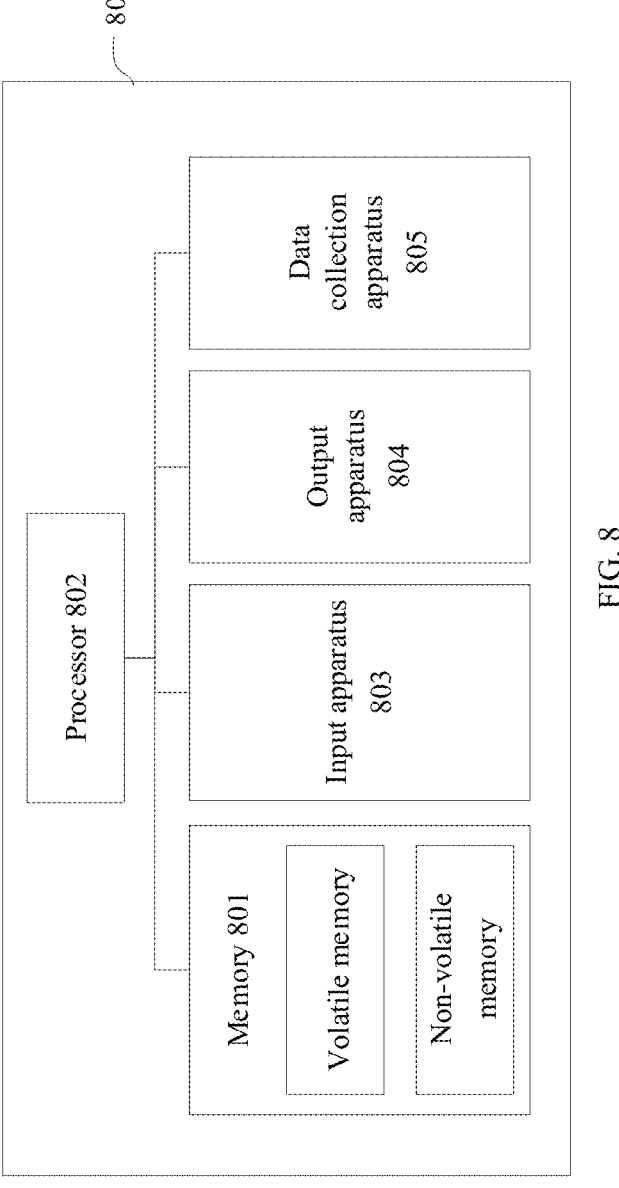
FIG. 8 is a schematic block diagram of an electronic device of the present disclosure.

Referring to FIG. 8, a block diagram of an electronic device 800 of an embodiment of the present disclosure is shown. As shown in FIG. 8, the electronic device 800 provided by the embodiment of the present disclosure may be configured to perform a method for acquiring a classification model or a method for determining a mutation category of the TERT gene promoter.

The electronic device 800 may include a memory 801, a processor 802, and a computer program stored on the memory and executable on the processor. The processor 802 is configured to perform the image processing method.

As shown in FIG. 8, in an embodiment, the electronic device 800 may completely include an input apparatus 803, an output apparatus 804, and a data collection apparatus 805. When performing the image processing method of the embodiment of the present disclosure, the data collection apparatus 805 may acquire the information of the multiple modalities. Then, the input apparatus 803 may acquire information of the multiple modalities of the data collection apparatus 805, and the information of the multiple modalities may be processed by the processor 802, which may specifically perform the above-mentioned method for acquiring a target model and the above-mentioned method for determining a prognosis evaluation value. The output apparatus 804 may output the target model or may output a result of the prognosis evaluation value output by the target model.

Of course, in an embodiment, the memory 801 may include a volatile memory and a non-volatile memory. The volatile memory may be understood to be a random-access memory configured to store and maintain data. The non-volatile memory refers to a computer memory in which the stored data does not disappear when the current is turned off. Of course, the computer program of the method for acquiring a target model or the method for determining a prognosis evaluation value of the present disclosure may be stored in both the volatile memory and the non-volatile memory, or in either one of the two.

Finally, it should be noted, relational terms such as "first" and "second" are used merely to distinguish an entity or operation from another entity or operation, and do not necessarily require or imply the existence of any such actual relationship or sequence between these entities or operations. Furthermore, the terms "comprising", "including" or any other variation thereof are intended to cover a non-exclusive inclusion, such that a process, method, article, or apparatus including a list of elements includes not only those elements but also other elements not expressly listed, or elements inherent to the process, method, article or apparatus. Without further limitations, an element defined by the phrase "comprising a . . . " does not exclude the presence of additional identical elements in the process, method, article or apparatus including said element.

The above is a detailed introduction to a method for acquiring a target model, a method for determining a prognosis evaluation value, a device, an apparatus and a medium provided by the present disclosure. Specific examples are used here to illustrate the principles and implementation methods of the present disclosure. The description of the above embodiments is only used to help understand the method and its core idea of the present disclosure. Moreover, for those skilled in the art, there will be changes in the specific implementation and application scope based on the ideas of the present application. In summary, the content of this description should not be understood as a limitation of the present application.

Other embodiments of the present disclosure will be readily apparent to those skilled in the art from consideration of the specification and practice of the application disclosed herein. This application is intended to cover any variations, uses, or adaptations of the application that follow the general principles of this application and include common knowledge or customary technical means in the technical field that are not disclosed in this application. The specification and examples be considered as exemplary only, and a true scope and spirit of the application is indicated by the following claims.

It is to be understood that the present disclosure is not limited to precise structures described above and illustrated in the accompanying drawings, and that various modifications and changes may be made without departing from the scope thereof. The scope of the application is limited only by the appended claims.

"One embodiment", "an embodiment" or "one or more embodiments" as used herein means that a particular feature, structure, or characteristic described in connection with the embodiments is included in at least one embodiment of the present disclosure. In addition, please note that examples of the word "in one embodiment" herein do not necessarily all refer to the same embodiment.

In the description provided herein, numerous specific details are set forth. However, it is understood that embodiments of the present disclosure may be practiced without these specific details. In some instances, common methods, structures and techniques have not been shown in detail in order not to obscure the understanding of this description.

In the claims, any reference signs placed between parentheses shall not be construed as limiting the claims. The word "comprising/including" does not exclude the presence of elements or steps not listed in the claim. The word "a" or "an" preceding an element does not exclude the presence of a plurality of such elements. The disclosure may be implemented by means of hardware including several distinct elements and a suitably programmed computer. In a unit claim enumerating several devices, several of these devices may be embodied by the same hardware item. The words such as "first", "second", and "third" as used do not indicate any order. These words may be interpreted as names.

Finally, it should be noted that the above embodiments are only used to illustrate the technical solution of the present disclosure, but not to limit it; although the present disclosure has been described in detail with reference to the foregoing embodiments, those of ordinary skill in the art should understand that it can still be modified, or equivalent substitutions may be made to some of the technical features; however, these modifications or substitutions do not cause the essence of the corresponding technical solutions to deviate from the spirit and scope of the technical solutions of the embodiments of the present disclosure.

The invention claimed is:

1. A method for acquiring a target model, comprising:
acquiring a plurality of sample groups, wherein each of the sample groups corresponds to a sample user, and comprises sample information of multiple modalities, and the sample information of the multiple modalities comprises at least two of a magnetic resonance (MR) sample image, clinical sample information, and gene sample information; and
obtaining a target model by performing iterative trainings on a preset model based on the plurality of sample groups, wherein the target model is used for predicting a prognosis evaluation value of a target object,
wherein each of the iterative trainings comprises:
performing, by using the preset model, feature extraction on the sample information of the multiple modalities in a current sample group respectively, and determining a predicted prognosis evaluation value and a consistency expression value based on extracted sample features, wherein the consistency expression value is used for characterizing a consistency degree of the sample features corresponding to a same target disease; and
updating parameters of the preset model based on the predicted prognosis evaluation value, a prognosis evaluation label corresponding to the current sample group, and the consistency expression value.

2. The method according to claim 1, wherein the updating parameters of the preset model based on the predicted prognosis evaluation value, a prognosis evaluation label corresponding to the current sample group, and the consistency expression value comprises:
acquiring a difference between the predicted prognosis evaluation value and the prognosis evaluation label; and
updating the parameters of the preset model with a target of minimizing the difference and maximizing the consistency expression value.

3. The method according to claim 2, wherein the updating the parameters of the preset model with a target of minimizing the difference and maximizing the consistency expression value comprises:
constructing a loss function based on the difference and the consistency expression value as follows:

$$\text{loss} = \sum_i (y'_i - y_i)^2 - \text{consistency};$$

and updating, based on a loss value of the loss function, the parameters of the preset model with the target of minimizing the difference and maximizing the consistency expression value,
wherein the 'loss' represents the loss value, $y'_i$ represents the predicted prognosis evaluation value, $y_i$ represents the prognosis evaluation label, and 'consistency' represents the consistency expression value.

4. The method according to claim 1, wherein the determining the consistency expression value based on extracted sample features comprises:

transposing each of the sample features, and obtaining transposed features corresponding to various sample features;

for two different sample features, fusing one of the two sample features with the transposed feature corresponding to the other sample feature, and obtaining a corresponding fused feature value; and determining the consistency expression value based on each fused feature value.

5. The method according to claim 1, wherein the sample information of each modality comprises a plurality of sub-sample information, and the performing, by using the preset model, feature extraction on the sample information of the multiple modalities in a current sample group comprises:

for the sample information of each modality, performing feature extraction on the plurality of sub-sample information in the sample information of the modality, and obtaining a plurality of sub-feature vectors corresponding to the plurality of sub-sample information; and obtaining a sample feature corresponding to the sample information of the modality by performing feature fusion on the plurality of sub-feature vectors corresponding to the sample information of each modality.

6. The method according to claim 5, wherein the obtaining a sample feature corresponding to the sample information of the modality by performing feature fusion on the plurality of sub-feature vectors corresponding to the sample information of each modality comprises:

determining an attention value between every two sub-feature vectors, the attention value is used for characterizing a degree of closeness between the two sub-feature vectors; and obtaining the sample feature corresponding to the sample information of the modality by fusing the plurality of sub-feature vectors based on the attention value.

7. The method according to claim 6, wherein the obtaining the sample feature corresponding to the sample information of the modality by fusing the plurality of sub-feature vectors based on the attention value comprises:

for each sub-feature vector, fusing all the other sub-feature vectors into the sub-feature vector based on attention values between the sub-feature vector and all the other sub-feature vectors, and obtaining a fused sub-vector for the sub-feature vector; and obtaining the sample feature corresponding to the sample information of the modality by performing re-fusion on a plurality of fused sub-vectors.

8. The method according to claim 6, wherein the parameters of the preset model comprise a first parameter matrix, the MR sample image comprises a plurality of slice sample images, and the determining an attention value between every two sub-feature vectors comprises:

for each slice sample image comprised in the MR sample image, determining an attention value between sub-feature vectors corresponding to every two slice sample images based on a current value of the first parameter matrix.

9. The method according to claim 5, wherein the parameters of the preset model comprise a second parameter matrix and a third parameter matrix, and the obtaining a sample feature corresponding to the sample information of the modality by performing feature fusion on the plurality of sub-feature vectors corresponding to the sample information of each modality comprises:

for each piece of clinical sub-sample information in the clinical sample information, performing feature fusion on sub-feature vectors corresponding to the clinical sub-sample information based on a current value of the second parameter matrix, and obtaining a sample feature corresponding to the clinical sample information; and for each piece of gene sub-sample information in the gene sample information, performing feature fusion on sub-feature vectors corresponding to the gene sub-sample information based on a current value of the third parameter matrix, and obtaining a sample feature corresponding to the gene sample information.

10. The method according to claim 1, wherein the parameters of the preset model comprise a parameter set corresponding to the clinical sample information, the clinical sample information comprises numerical sub-sample information and non-numerical sub-sample information, and the performing, by using the preset model, feature extraction on the sample information of the multiple modalities in a current sample group comprises:

for the clinical sample information in the current sample group, converting the non-numerical sub-sample information into a first sub-feature vector;

obtaining a corresponding second sub-feature vector by mapping, based on a current value of each parameter in the parameter set, the numerical sub-sample information to a target space, wherein the parameters in the parameter set are used for determining a dimension of the target space and a value at each spatial point; and obtaining a sample feature corresponding to the clinical sample information by fusing the first sub-feature vector and the second sub-feature vector.

11. The method according to claim 10, wherein the parameter set comprises a first parameter vector, a second parameter vector, and a fourth parameter matrix, and the obtaining a corresponding second sub-feature vector by mapping, based on a current value of each parameter in the parameter set, the numerical sub-sample information to a target space comprises:

mapping the numerical sub-sample information to a first dimension in the target space based on a current value of the first parameter vector to obtain a mapping value of the first dimension, wherein the first parameter vector is used for determining a value of a spatial point of the target space in the first dimension; and determining the second sub-feature vector based on the mapping value of the first dimension, a current value of the second parameter vector, and a current value of the fourth parameter matrix, wherein the second parameter vector is used for determining a value of a spatial point of the target space in a second dimension, and the fourth parameter matrix is used for assigning a parameter to each spatial position in the first dimension and the second dimension.

12. The method according to claim 11, wherein the parameter set further comprises a plurality of third parameter vectors, and after determining the second sub-feature vector based on the mapping value of the first dimension, the current value of the second parameter vector, and the current value of the fourth parameter matrix, the method further comprises:

correcting, based on the second sub-feature vector and the plurality of third parameter vectors, the second sub-feature vector according to a formula as follows:

$$va = \frac{e^{\left(sa^T \cdot a_1\right)}}{\sum_{i=1}^{3} e^{\left(sa^T \cdot a_i\right)}} \times a_1 + \frac{e^{\left(sa^T \cdot a_2\right)}}{\sum_{i=1}^{3} e^{\left(sa^T \cdot a_i\right)}} \times a_2 + \frac{e^{\left(sa^T \cdot a_3\right)}}{\sum_{i=1}^{3} e^{\left(sa^T \cdot a_i\right)}} \times a_3,$$

wherein va is a corrected second sub-feature vector, sa is the second sub-feature vector, and $a_1$, $a_2$, and $a_3$ are the third parameter vectors; and the obtaining a sample feature corresponding to the clinical sample information by fusing the first sub-feature vector and the second sub-feature vector comprises:

obtaining the sample feature corresponding to the clinical sample information by fusing the first sub-feature vector and the corrected second sub-feature vector.

13. The method according to claim 1, wherein the parameters of the preset model comprise a dimension parameter matrix corresponding to sample information of each modality, and the determining a predicted prognosis evaluation value and a consistency expression value based on extracted sample features comprises:

obtaining a converted sample feature by performing, based on the sample feature and the dimension parameter matrix corresponding to the sample information of each modality, dimension transformation on the sample feature corresponding to the sample information of the modality; and determining the predicted prognosis evaluation value and the consistency expression value based on converted sample features corresponding to each piece of the sample information of the multiple modalities.

14. The method according to claim 1, wherein the preset model comprises a fusion module, a prediction branch, a consistency expression branch, and data processing modules corresponding to sample information of the modalities, and the performing, by using the preset model, feature extraction on the sample information of the multiple modalities in a current sample group, and determining a predicted prognosis evaluation value and a consistency expression value based on extracted sample features comprises:

for the sample information of each modality in the current sample group, performing feature extraction on corresponding sample information using a data processing module corresponding to the sample information of the modality;

fusing sample features output by the data processing modules using the fusion module;

determining, using the prediction branch, the predicted prognosis evaluation value corresponding to a feature output by the fusion module; and determining, using the consistency expression branch, the consistency expression value corresponding to the sample features output by the data processing modules.

15. A method for determining a prognosis evaluation value, comprising:

acquiring information of multiple modalities of an object to be measured, wherein the information of the multiple modalities comprises a magnetic resonance (MR) image, clinical information, and gene information; and obtaining a prognosis evaluation value of the object to be measured by inputting the information of the multiple modalities into a target model, wherein the target model is obtained according to the method according to claim 1.

16. An apparatus for acquiring a target model, comprising:

a processor, and a memory storing a computer program that, when executed by the processor, implements the method for acquiring a target model according to claim 1.

17. An apparatus for determining a prognosis evaluation value, comprising:

a processor, and a memory storing a computer program that, when executed by the processor, implements the method for determining a prognosis evaluation value according to claim 15.

18. A non-transitory computer readable storage medium storing a computer program that, when executed by a processor, causes the processor to implement the method for acquiring a target model according to claim 1.

19. A non-transitory computer readable storage medium storing a computer program that, when executed by a processor, causes the processor to implement the method for determining a prognosis evaluation value according to claim 15.

* * * * *